(12) United States Patent
 Sevenants

(10) Patent No.: US 11,649,654 B2
(45) Date of Patent: May 16, 2023

(54) TANK WITH DOOR LOCKING MECHANISM

(71) Applicant: Pall Corporation, Port Washington, NY (US)

(72) Inventor: Jorrit Sevenants, Tienen (BE)

(73) Assignee: Cytiva US LLC, Marlborough, MA (US)

( * ) Notice: Subject to any disclaimer, the term of this patent is extended or adjusted under 35 U.S.C. 154(b) by 363 days.

(21) Appl. No.: 17/067,991

(22) Filed: Oct. 12, 2020

(65) Prior Publication Data
 US 2022/0112740 A1   Apr. 14, 2022

(51) Int. Cl.
 *E05B 7/00*  (2006.01)
 *B65D 90/04* (2006.01)
 *C12M 1/00*  (2006.01)

(52) U.S. Cl.
 CPC .............. *E05B 7/00* (2013.01); *B65D 90/046* (2013.01); *C12M 23/14* (2013.01)

(58) Field of Classification Search
 CPC .. E05B 7/00; E05B 5/00; B65D 90/00; B65D 90/04; B65D 90/046; B65D 90/047; B65D 90/048; B65D 88/1606; B65D 88/1612; C12M 23/00; C12M 23/14
 USPC ...................................... 292/336.3
 See application file for complete search history.

(56) References Cited

U.S. PATENT DOCUMENTS

| | | | |
|---|---|---|---|
| 6,644,165 B1 | 11/2003 | King | |
| 6,749,235 B1 | 6/2004 | Crisp | |
| 6,929,292 B1 * | 8/2005 | Galindo | E05B 65/0014 292/288 |
| 8,177,268 B2 | 5/2012 | Varney et al. | |
| 9,611,674 B2 | 4/2017 | Cox et al. | |
| 9,675,947 B2 | 6/2017 | Gebauer et al. | |
| 10,227,799 B1 | 3/2019 | Hallsten et al. | |
| 10,947,489 B2 | 3/2021 | Husemann et al. | |
| 2015/0083614 A1 * | 3/2015 | Cox | E05B 17/2038 292/164 |
| 2016/0022523 A1 | 1/2016 | Bartlett | |
| 2017/0051239 A1 * | 2/2017 | Knight | B01F 27/0723 |
| 2018/0187140 A1 | 7/2018 | Husemann et al. | |
| 2018/0318823 A1 | 11/2018 | Baumgaertner et al. | |
| 2019/0078351 A1 * | 3/2019 | Marsden | E05B 13/002 |

FOREIGN PATENT DOCUMENTS

| | | |
|---|---|---|
| CN | 209924613 U | 1/2020 |
| CN | 210735100 U | 6/2020 |
| CN | 111442868 A | 7/2020 |
| DE | 10 2015 007 060 A1 | 12/2016 |
| JP | 2012-219583 A | 11/2012 |
| WO | WO 2001/021914 A1 | 3/2001 |
| WO | WO 2019/053512 A1 | 3/2019 |

OTHER PUBLICATIONS

Japanese Patent Office, Office Action issued in counterpart Japanese Patent Application No. 2021-153333, dated Sep. 6, 2022.

(Continued)

*Primary Examiner* — Nathan Cumar
(74) *Attorney, Agent, or Firm* — Leydig, Voit & Mayer, Ltd.

(57) ABSTRACT

A tank with a door locking mechanism for use in bioprocessing, and methods of using the door locking mechanism, is provided.

12 Claims, 12 Drawing Sheets

(56) References Cited

OTHER PUBLICATIONS

Singapore Intellectual Property Office, Search Report issued in counterpart Singapore Patent Application No. 10202110206R, dated Nov. 10, 2022.

European Patent Office, Extended European Search Report issued in counterpart European Patent Application No. 21197365.6, dated Mar. 24, 2022.

"TM-10-101-24 Transom Door Latch," accessed online at <southco.com/en_us_int/latches/entry-door-latches-locks/swing-action-latches/tm-swim-door-latch/tm-10-101-24>, on Sep. 29, 2020.

* cited by examiner

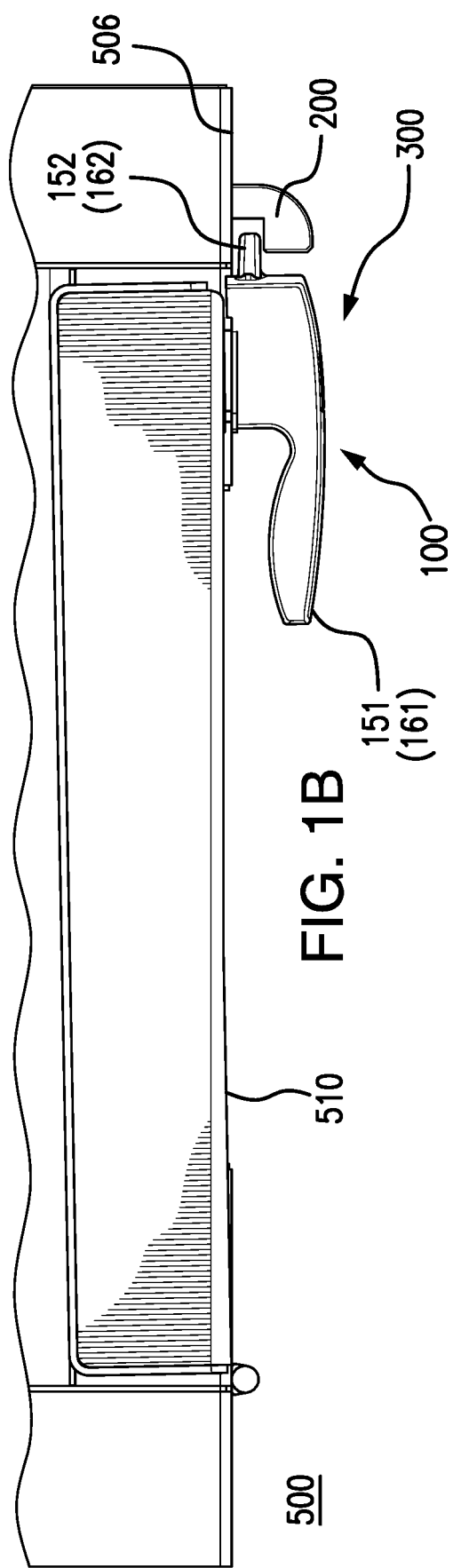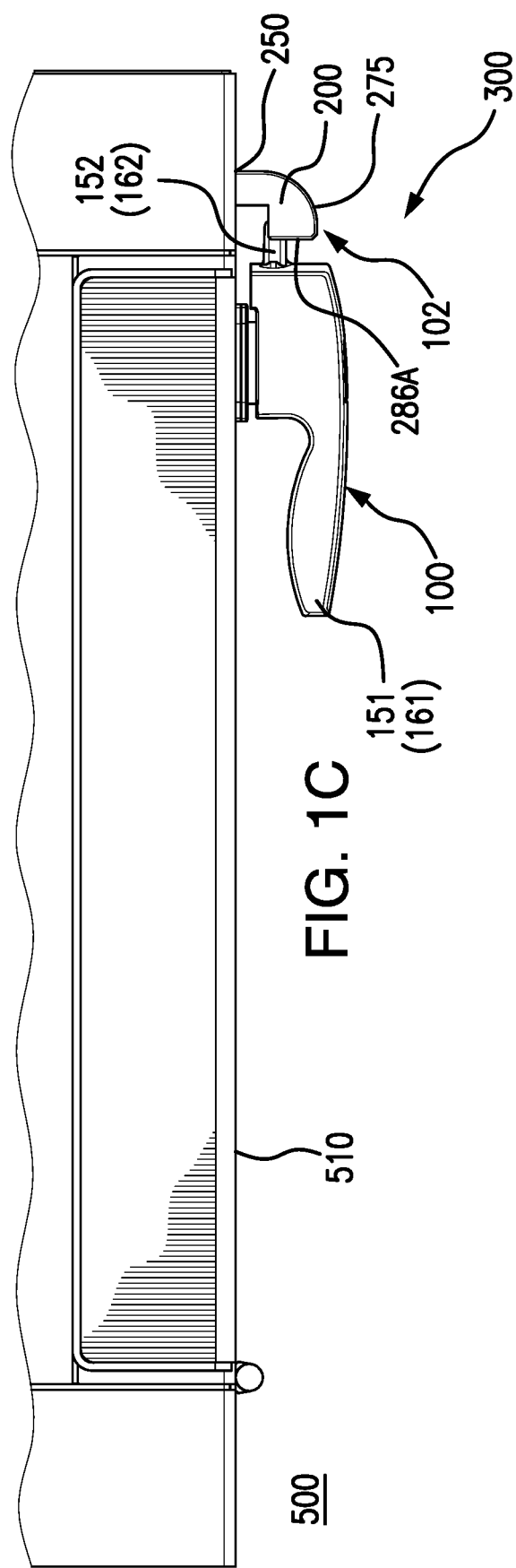

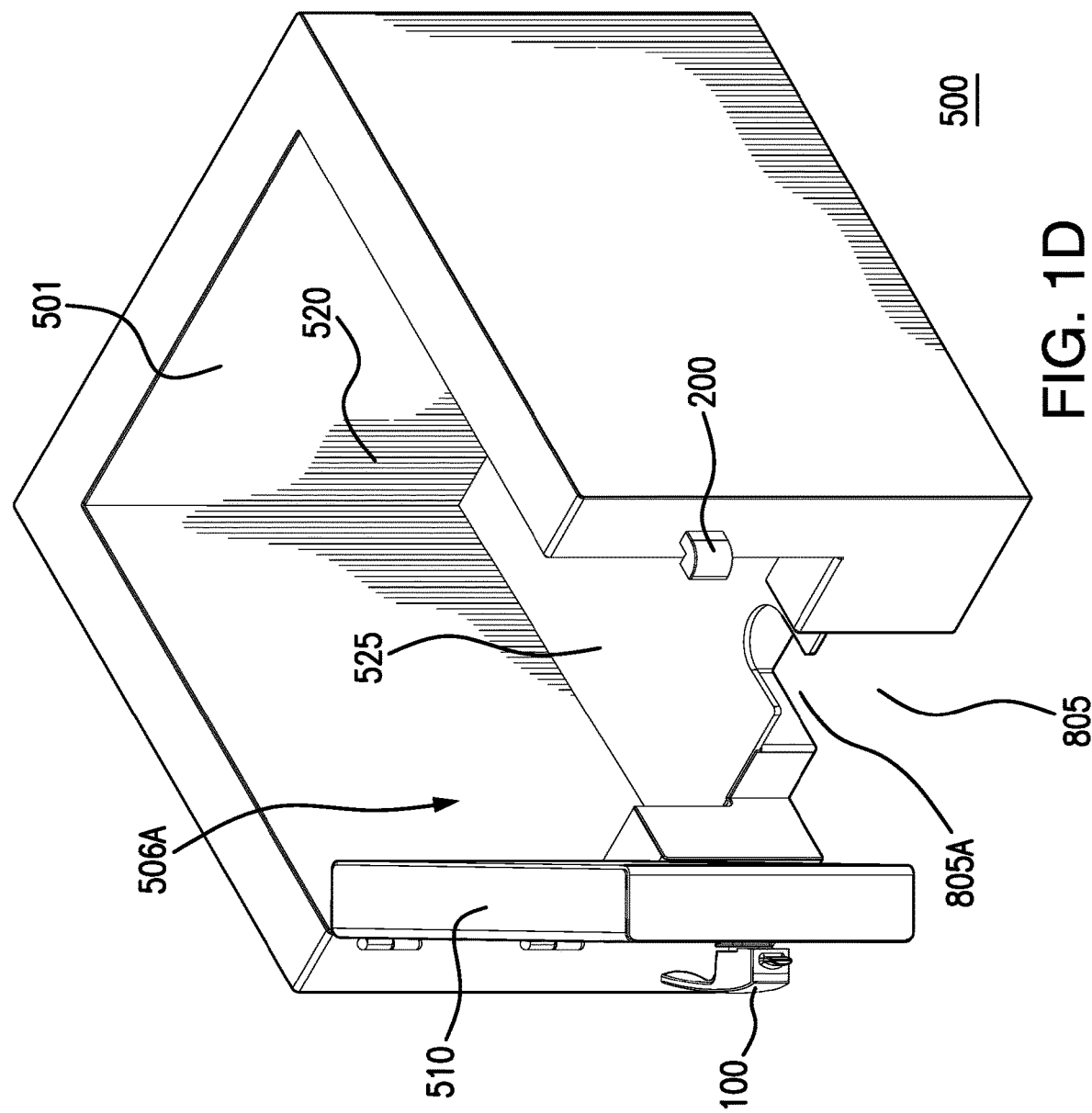

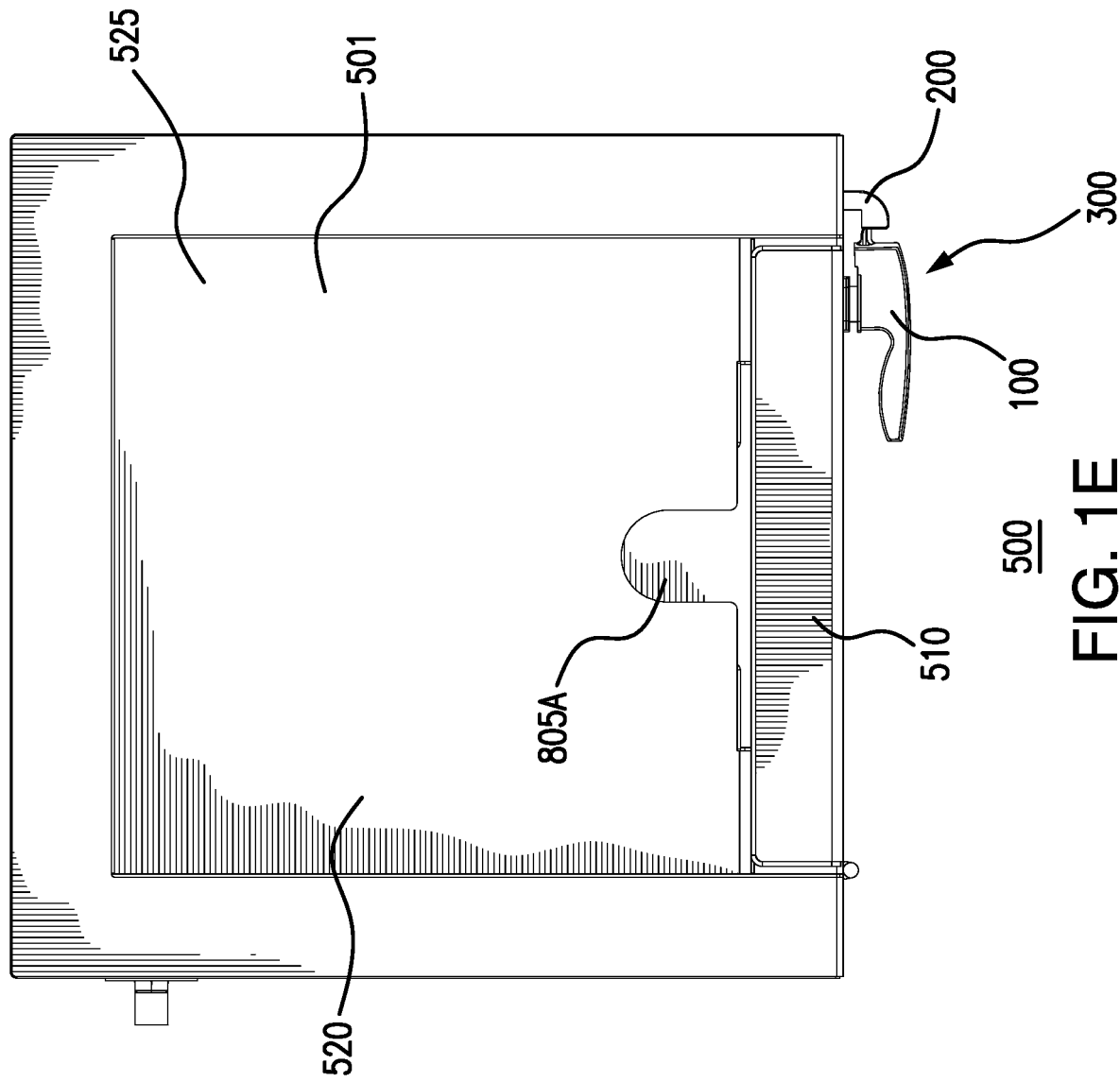

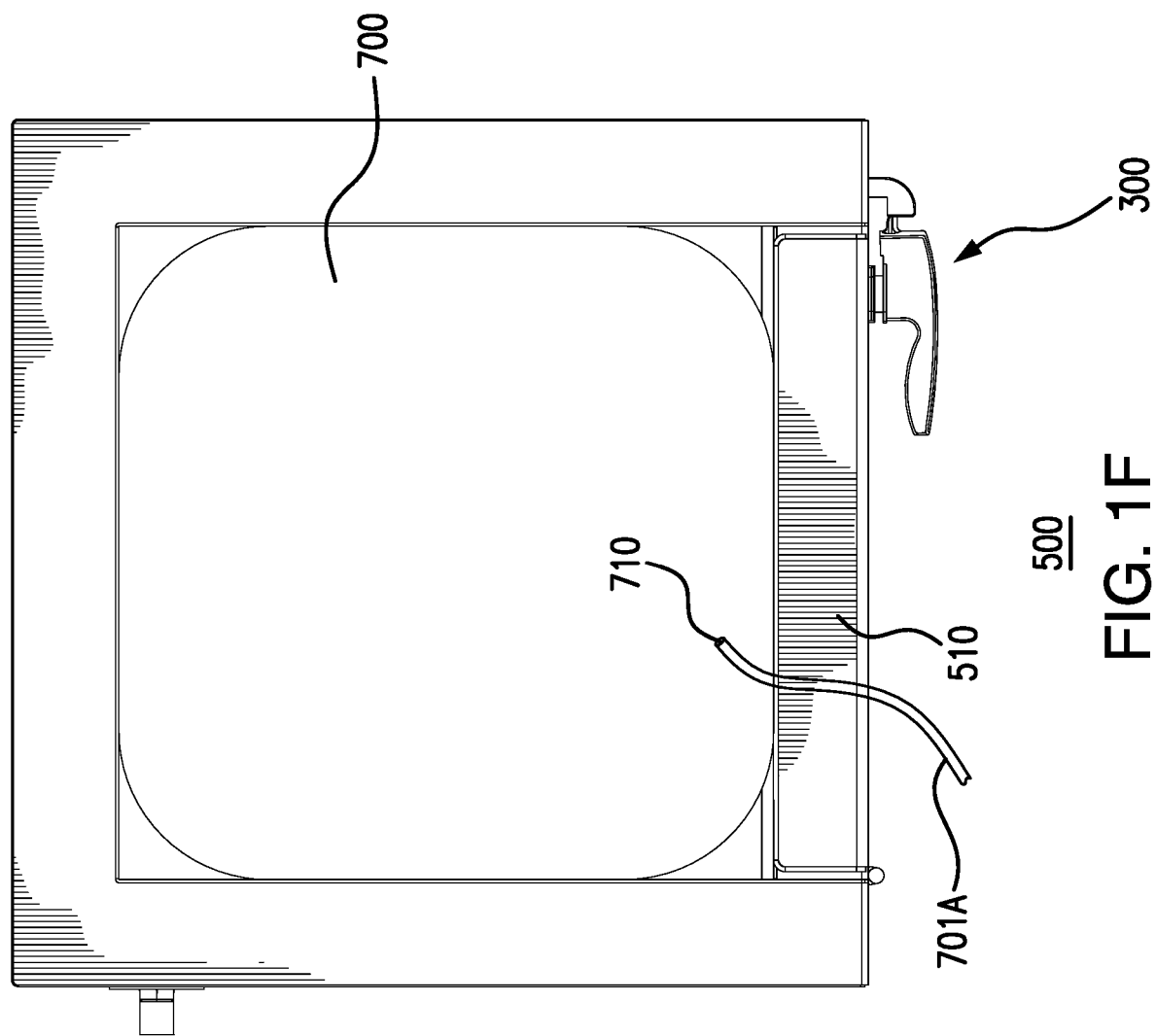

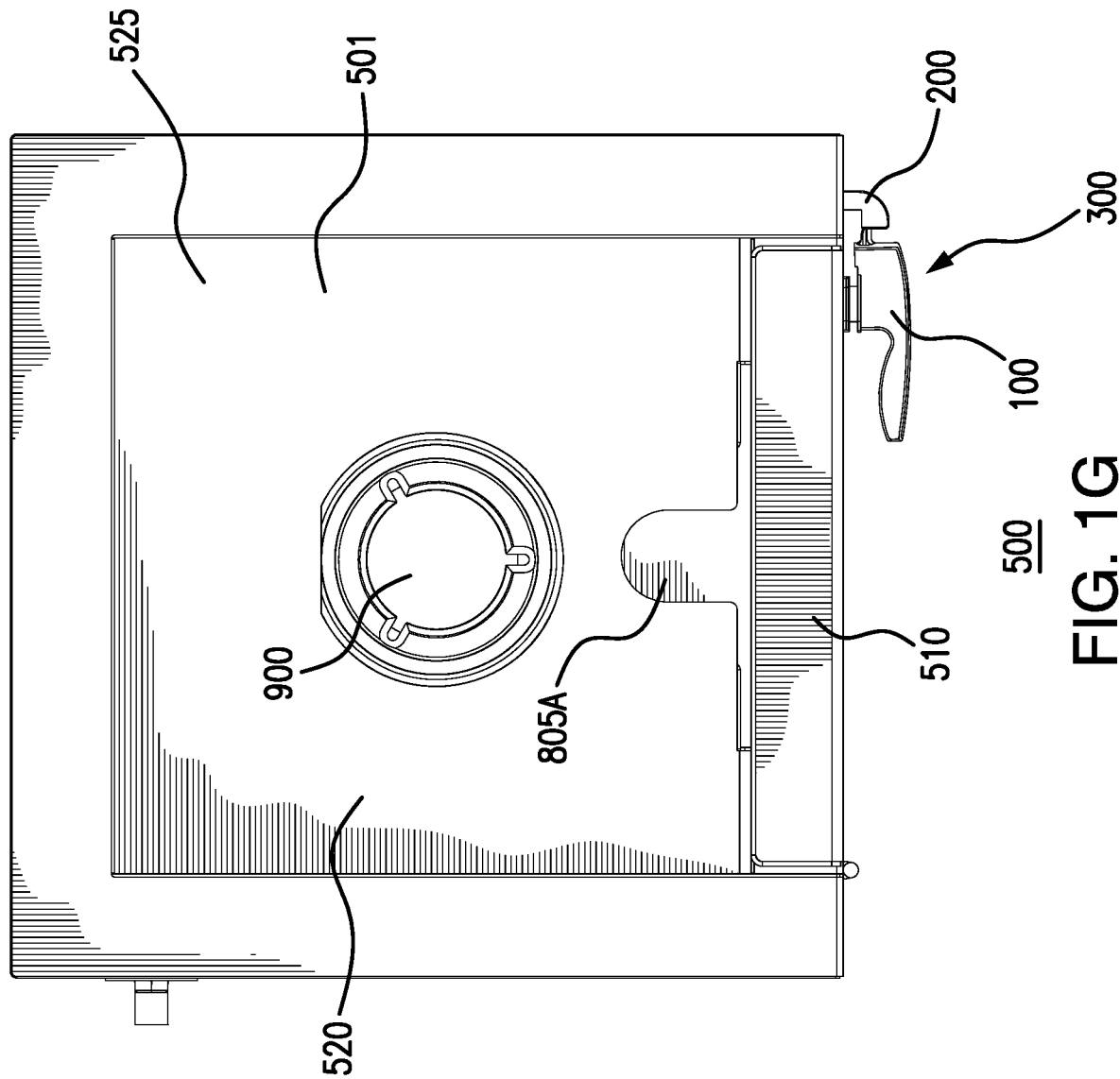

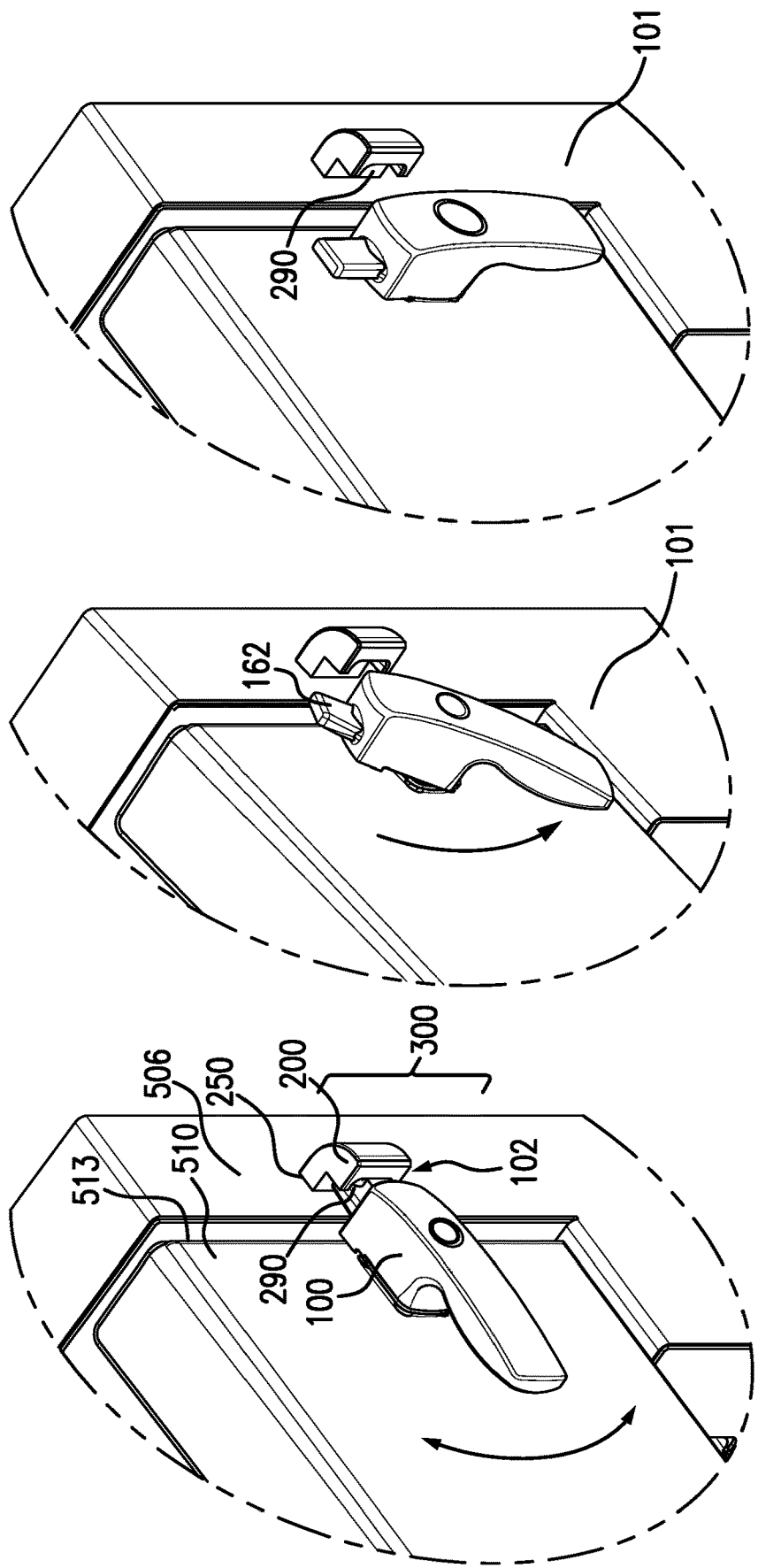

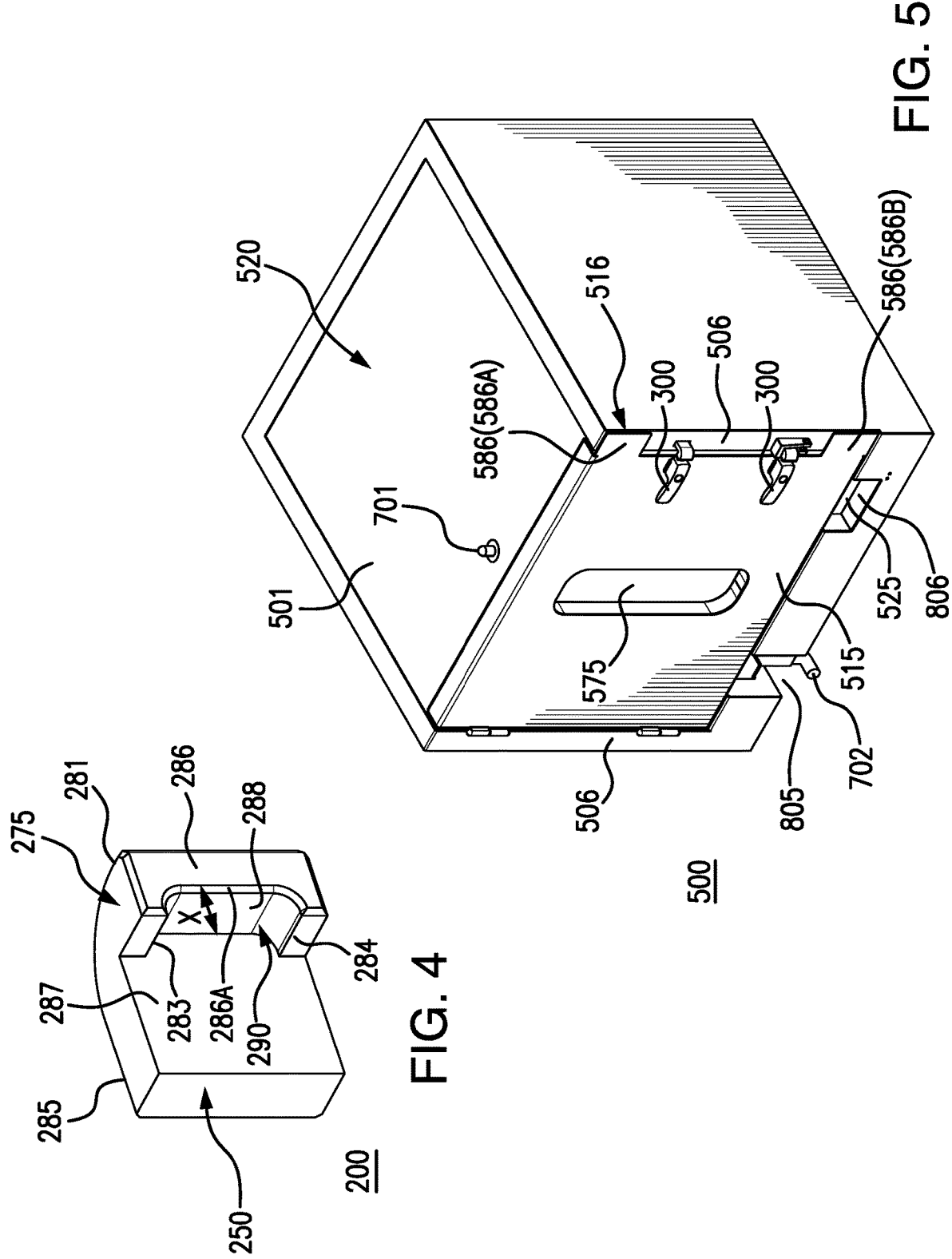

TANK WITH DOOR LOCKING MECHANISM

BACKGROUND OF THE INVENTION

Tanks are used in a variety of bioprocessing applications. For example, a flexible container such as a bag can be placed in the tank, the door to the tank is closed and latched, and the bag is filled as part of the bioprocessing application.

However, there is a need for improved latches for tanks that receive flexible containers for bioprocessing applications.

The present invention provides for ameliorating at least some of the disadvantages of the prior art. These and other advantages of the present invention will be apparent from the description as set forth below.

BRIEF SUMMARY OF THE INVENTION

An aspect of the invention provides a tank with a door locking mechanism comprising: (a) a tank comprising a bottom wall, first and second opposing side walls, a rear wall, an outwardly pivoting tank door, a front wall having an opening, and a hinge mounted to the front wall and the outwardly pivoting tank door, wherein the outwardly pivoting tank door is arranged to cover at least a portion of the opening, the tank having an interior cavity for receiving an expandable bioprocessing container having flexible walls; the tank including a door locking mechanism comprising: (i) a rotatable shaft mounted to the outwardly pivoting tank door, the rotatable shaft having a first end and a second end, the second end comprising a projecting arm; and, (ii) an arm receiver, comprising a base mounted to the front wall of the tank at a distance from the outwardly pivoting tank door and the rotatable shaft, the arm receiver further comprising a receiver top extending horizontally from the base, the receiver top comprising a receiver top wall, first and second opposing receiver top side walls, a receiver top rear wall, and a receiver top front wall having a bottom end, the receiver top opposing side walls each extending toward the base a distance past the bottom end of the receiver top front wall; the bottom end of the receiver top front wall and first and second opposing receiver top side walls defining an arm receiver opening for receiving the projecting arm when the rotatable shaft is rotated to align the projecting arm with the arm receiver opening, and the outwardly pivoting tank door pivots outwardly upon being contacted by an expanded bioprocessing container.

Another aspect of the invention comprises a tank with a door locking mechanism comprising (a) a tank comprising a housing having an interior cavity for receiving an expandable bioprocessing container having flexible walls; a bottom wall; a side wall, wherein the side wall has an opening; an outwardly pivoting tank door; and a hinge mounted to the side wall and the outwardly pivoting tank door, wherein the outwardly pivoting tank door is arranged to cover at least a portion of the opening; the tank including a door locking mechanism comprising: (i) a rotatable shaft mounted to the outwardly pivoting tank door, the rotatable shaft having a first end and a second end, the second end comprising a projecting arm; and, (ii) an arm receiver, comprising a base mounted to the at least one side wall of the tank at a distance from the outwardly pivoting tank door and the rotatable shaft, the arm receiver further comprising a receiver top extending horizontally from the base, the receiver top comprising a receiver top wall, first and second opposing receiver top side walls, a receiver top rear wall, and a receiver top front wall having a bottom end, the receiver top opposing side walls each extending toward the base a distance past the bottom end of the receiver top front wall; the bottom end of the receiver top front wall and first and second opposing receiver top side walls defining an arm receiver opening for receiving the projecting arm when the rotatable shaft is rotated to align the projecting arm with the arm receiver opening, and the outwardly pivoting tank door pivots outwardly upon being contacted by an expanded bioprocessing container.

In another aspect, a method of operating the tank with the door locking mechanism is provided. In a preferred aspect, the method comprises placing a bioprocessing container with flexible walls into the interior cavity of an aspect of the tank; rotating the rotatable shaft until the projecting arm aligns with the arm receiver opening; inflating the bioprocessing container with air or gas and/or filling the bioprocessing container with fluid until the bioprocessing container expands and a flexible wall of the expanded bioprocessing container contacts the pivoting tank door and the pivoting tank door pivots outwardly.

BRIEF DESCRIPTION OF THE SEVERAL VIEWS OF THE DRAWING(S)

FIG. 1A is a front perspective view of a tank including a door locking mechanism comprising a rotatable shaft comprising a handle and a projecting arm; and an arm receiver; mounted to the tank according to an aspect of the invention, wherein the tank door is pivoted outwardly and the door locking mechanism and the tank door are locked with the projecting arm received by the arm receiver; FIG. 1B is top view of a door locking mechanism, wherein the rotatable shaft is attached to a hinged tank door, and the arm receiver is attached to the front wall of the tank, wherein the projecting arm is not received in the arm receiver; FIG. 1C is top view of a door locking mechanism shown in FIG. 1A, wherein the tank door is pivoted outwardly and the door locking mechanism and the tank door are locked with the projecting arm received by the arm receiver; FIG. 1D is a perspective view of the tank shown in FIG. 1A, with the tank door partially open; FIG. 1E is a top view of the tank shown in FIG. 1A, with the tank door closed; FIG. 1F is a top view of the tank shown in FIG. 1A, also showing an expanded bioprocessing container in the tank contacting the tank door and causing the tank door to pivot outwardly; and FIG. 1G is a top view of another tank similar to that shown in FIG. 1A, wherein the floor of the tank includes an opening allowing the insertion of a removable mixer drive unit, or for mounting a mixer.

FIG. 3 shows rotation of the rotatable shaft upwardly and downwardly.

FIG. 4 shows a perspective view of the arm receiver of the door locking mechanism shown in FIGS. 1A and 1B.

FIG. 5 shows a perspective of view of a tank with opposing side walls and including two door locking mechanisms according to an aspect of the invention, also showing upper and lower door stops preventing the door from pivoting into the interior cavity of the tank, and showing cutouts for tubing and/or ports connected to a bioprocessing container that can be placed in the tank.

FIGS. 6A-6C show filling of a bioprocessing container in the tank, wherein FIG. 6A shows fluid initially entering the container, FIG. 6B shows the container approximately halfway filled, and FIG. 6C shows the container filled.

DETAILED DESCRIPTION OF THE INVENTION

Figure 1A:
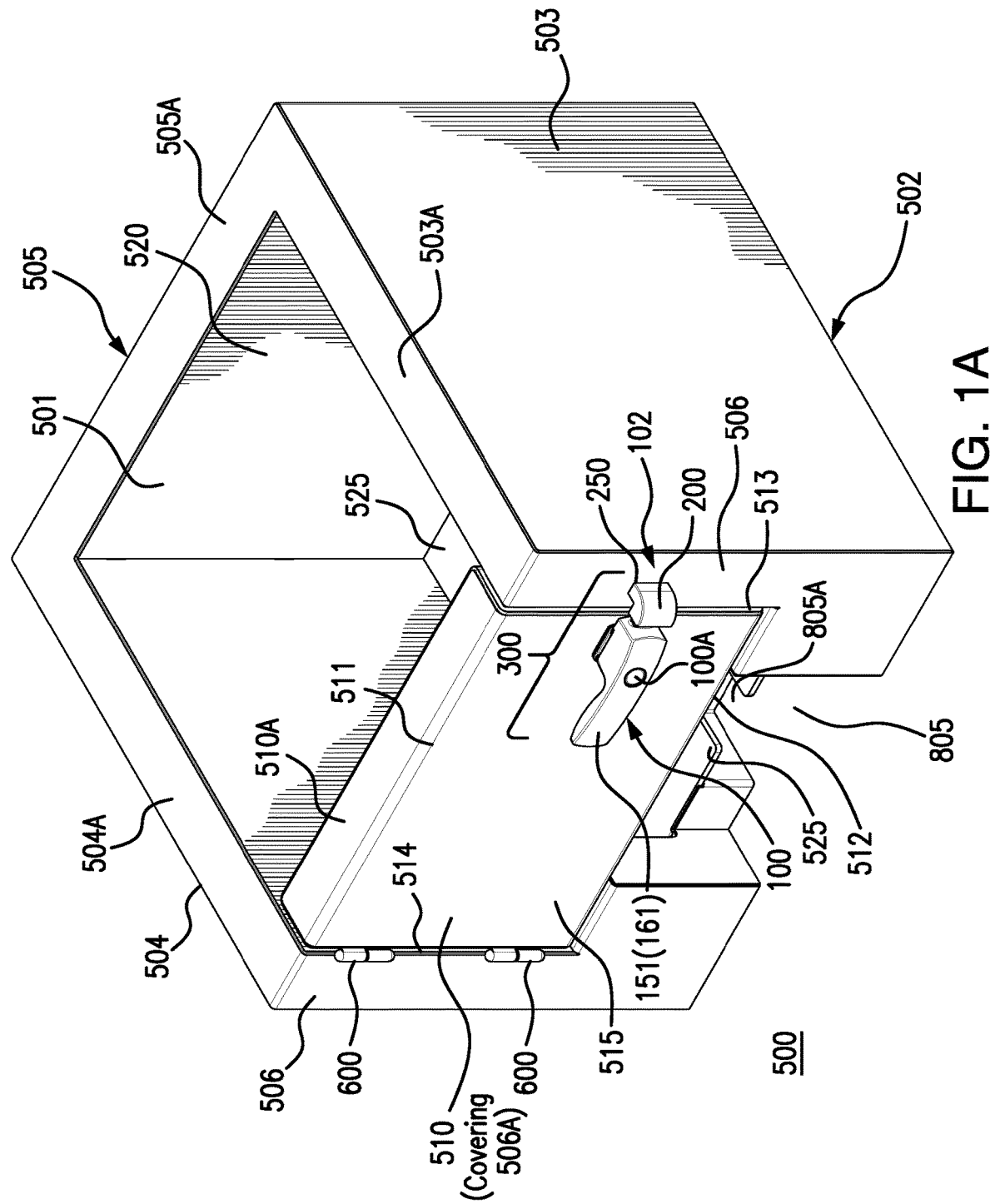

In accordance with an aspect of the invention, a tank with a door locking mechanism comprises: (a) a tank comprising a bottom wall, first and second opposing side walls, a rear wall, an outwardly pivoting tank door, a front wall having an opening, and a hinge mounted to the front wall and the outwardly pivoting tank door, wherein the outwardly pivoting tank door is arranged to cover at least a portion of the opening, the tank having an interior cavity for receiving an expandable bioprocessing container with flexible walls; the tank including a door locking mechanism comprising: (i) a rotatable shaft mounted to the outwardly pivoting tank door, the rotatable shaft having a first end and a second end, the second end comprising a projecting arm; and, (ii) an arm receiver, comprising a base mounted to the front wall of the tank at a distance from the outwardly pivoting tank door and the rotatable shaft, the arm receiver further comprising a receiver top extending horizontally from the base, the receiver top comprising a receiver top wall, first and second opposing receiver top side walls, a receiver top rear wall, and a receiver top front wall having a bottom end, the receiver top opposing side walls each extending toward the base a distance past the bottom end of the receiver top front wall; the bottom end of the receiver top front wall and first and second opposing receiver top side walls defining an arm receiver opening for receiving the projecting arm when the rotatable shaft is rotated to align the projecting arm with the arm receiver opening, and the outwardly pivoting tank door pivots outwardly upon being contacted by an expanded bioprocessing container.

In accordance with another aspect of the invention a tank with a door locking mechanism is provided comprising (a) a tank comprising a housing having an interior cavity for receiving an expandable bioprocessing container having flexible walls; a bottom wall; a side wall, wherein the side wall has an opening; an outwardly pivoting tank door; and a hinge mounted to the side wall and the outwardly pivoting tank door, wherein the outwardly pivoting tank door is arranged to cover at least a portion of the opening; the tank including a door locking mechanism comprising: (i) a rotatable shaft mounted to the outwardly pivoting tank door, the rotatable shaft having a first end and a second end, the second end comprising a projecting arm; and, (ii) an arm receiver, comprising a base mounted to the at least one side wall of the tank at a distance from the outwardly pivoting tank door and the rotatable shaft, the arm receiver further comprising a receiver top extending horizontally from the base, the receiver top comprising a receiver top wall, first and second opposing receiver top side walls, a receiver top rear wall, and a receiver top front wall having a bottom end, the receiver top opposing side walls each extending toward the base a distance past the bottom end of the receiver top front wall; the bottom end of the receiver top front wall and first and second opposing receiver top side walls defining an arm receiver opening for receiving the projecting arm when the rotatable shaft is rotated to align the projecting arm with the arm receiver opening, and the outwardly pivoting tank door pivots outwardly upon being contacted by an expanded bioprocessing container.

In some aspects, the tank door includes at least one extension providing a door stop preventing the tank door from entering the internal cavity of the tank.

Aspects of the door locking mechanism can be manually and/or electronically controlled. Preferably, the door locking mechanism is manually controlled without automation or electronics, thus reducing complexity and cost.

Tanks can include any number of door locking mechanisms.

In another aspect, a method of operating the tank with the door locking mechanism is provided, the method comprising placing a bioprocessing container with flexible walls into the interior cavity of an aspect of the tank; rotating the rotatable shaft until the projecting arm aligns with the arm receiver opening; and, inflating the bioprocessing container with air or gas and/or filling the bioprocessing container with fluid until the bioprocessing container expands and a flexible wall of the expanded bioprocessing container contacts the pivoting tank door and the pivoting tank door pivots outwardly. In some aspects, the bioprocessing container is inflated with air or gas followed by filling with liquid.

In a preferred aspect, method includes pivoting the pivoting door outwardly until the projecting arm contacts the bottom end of receiver top bottom wall.

Advantageously, since a user is unable to open a tank when the container inside the tank is at least partially filed, possible injury to the user is avoided. If desired, an external lock can be attached to the locked door locking mechanism to reduce the chance that the door would open during transport and/or to prevent unauthorized opening.

Door locking mechanisms can be used with a variety of tanks, including commercially available tanks. Tanks can have more than 1 door, as shown in, for example, FIG. 7, and/or tanks can have any suitable shape, including rounded, with a curved door, as shown in, for example, FIG. 8.

Each of the components of the invention will now be described in more detail below, wherein like components have like reference numbers.

FIG. 1A is a perspective view of a tank 500 (also shown in FIGS. 1D-1G, and 5) including a door locking mechanism 300 according to an aspect of the invention, wherein the tank door is closed, FIG. 1D is perspective view of the tank 500 including the door mechanism as shown in FIG. 1A, wherein the door is partially open.

The illustrated aspect of the tank 500 in FIG. 1A comprises an open top 501 (if desired, the tank can include a top wall (not shown); a bottom wall 502, first and second opposing side walls 503, 504, a rear wall 505 (having top walls 503A, 504A, and 505A, respectively), an outwardly pivoting tank door 510 (having a top wall 510A; in some aspects wherein the tank includes a top wall, the tank door does not provide part of the top wall of the tank), a front wall 506 having an opening 506A, and at least one hinge 600 (two hinges are shown) mounted to the front wall and the outwardly pivoting tank door, wherein the outwardly pivoting tank door is arranged to cover at least a portion of the opening, the tank having an interior cavity 520 for receiving an expandable bioprocessing container 700 (see, FIGS. 1F and 6A-6C) with flexible walls, the interior cavity having a floor 525.

Typically, as shown in FIGS. 1A, 1D, and 5, the lower portion of the tank extends below floor 525 of the interior cavity 520, providing a base for the tank. If desired, the opening 506A can be larger than the tank door 510, e.g., due to small gaps between the door and the door opening, and due to space below the bottom of the door. However, the tank door 510 covers a major portion (e.g., at least about 60%, and in some embodiments, at least about 80% of the area) of the opening 506A.

The illustrated door locking mechanism 300 comprises a rotatable shaft 100 (rotatable between a first (unlocked) position 101 (see, FIG. 3) and a second (locked) position 102 (see, FIGS. 1A, 1C, and 3)) mounted to the outwardly pivoting tank door 510, the rotatable shaft having a first end 151 comprising a handle 161 and a second end 152 comprising a projecting arm 162; and, an arm receiver 200 (see, FIG. 4), comprising a base 250 mounted to the front wall 506 of the tank 500 at a distance from the outwardly pivoting tank door 510 and the rotatable shaft 100, the arm receiver 200 further comprising a receiver top 275 extending horizontally from the base, the receiver top comprising a receiver top wall 281, inner walls 287 and 288, first and second opposing receiver top side walls 283, 284, a receiver top rear wall 285, and a receiver top front wall 286 having a bottom end 286A, the receiver top opposing side walls each extending toward the base a distance "X" past the bottom end of the receiver top front wall; the bottom end of the receiver top front wall and first and second opposing receiver top side walls defining an arm receiver opening 290 for receiving the projecting arm when the rotatable shaft is rotated to align the projecting arm with the arm receiver opening, and the outwardly pivoting tank door pivots outwardly (see, FIGS. 1B, 1C, and 1F) upon being contacted by an expanded bioprocessing container.

The tank door 510 has a top end 511, bottom end 512, front end 513, a rear end 514, an outer surface 515 and an inner surface 516 (see, FIG. 5; in some aspects, the inner surface of the door does not contact the tank, e.g., as in FIGS. 1A-1C, and 1E-1G); and at least one hinge 600 mounted to the door 510 (two hinges are illustrated as mounted to an edge of the rear end 514 and on the outer surface of the front wall 506 of the tank). Aspects of the invention can have a plurality of hinges; typically, if there is a single hinge, it may mounted approximately half way between the top and bottom ends of the door.

Figure 7:
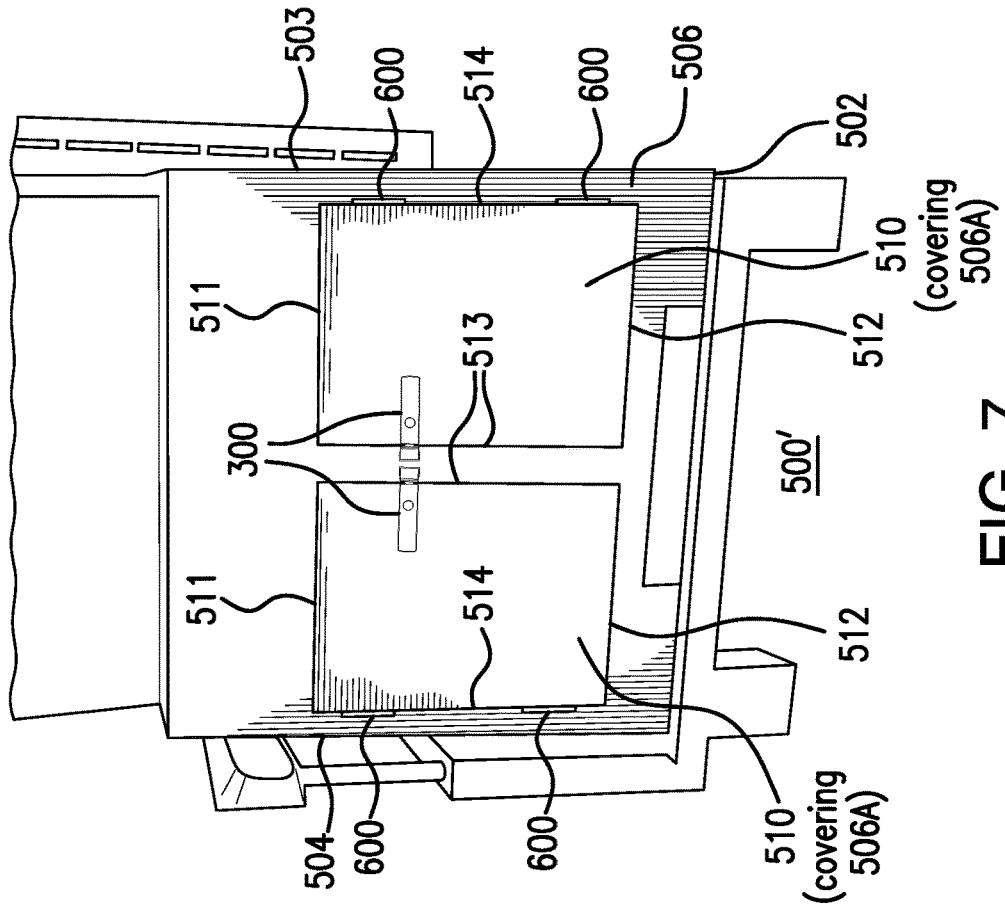
FIG. 7 is a perspective view of a tank with opposing side walls and two doors and including a door locking mechanism associated with each door according to an aspect of the invention.

FIG. 7 illustrates a tank 500' according to another aspect of the invention, similar to the illustrated aspect of the tank 500 shown in FIG. 1A, however, tank 500' includes a pair of outwardly pivoting tank doors 510 (each covering an opening 506A) and a corresponding pair of door locking mechanisms 300 as described above. The interior cavity and interior cavity floor are not shown.

Figure 8:
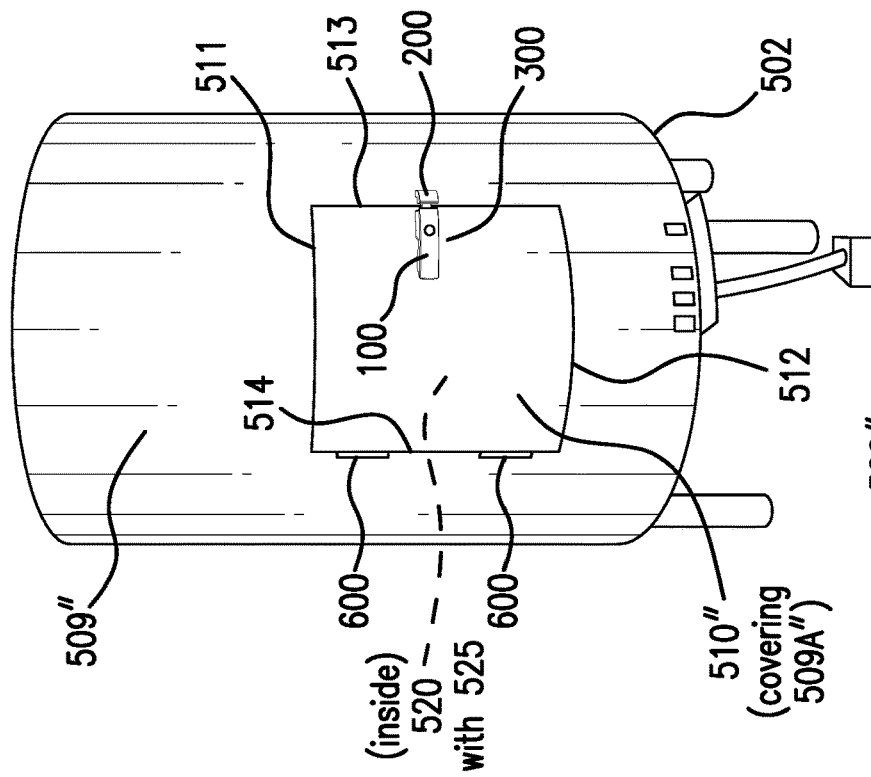
FIG. 8 is a perspective view of a tank with a continuous curved side wall and including a door locking mechanism according to an aspect of the invention.

As noted above, tanks can have any suitable shape. FIG. 8 illustrates a tank 500" according to another aspect of the invention, including an outwardly pivoting tank door 510", and a door locking mechanism 300 as described above. However, in contrast with tanks 500 and 500', tank 500" has a rounded shape with a continuous curved side wall 509" and the outwardly pivoting tank door 510" is curved (and covers opening 509A"). With the exception of outwardly pivoting tank door 510" being curved, the tank door 510" is similar in structure to outwardly pivoting tank door 510 as described above. The views of the interior cavity 520 for receiving an expandable bioprocessing container 700 with flexible walls, wherein the interior cavity has a floor 525, are blocked by the door 510".

Aspects of the invention can have any number of door locking mechanisms 300. Typically, if there is a single door locking mechanism, the rotatable shaft may be mounted approximately half way between the top and bottom ends of the door.

Figure 2:
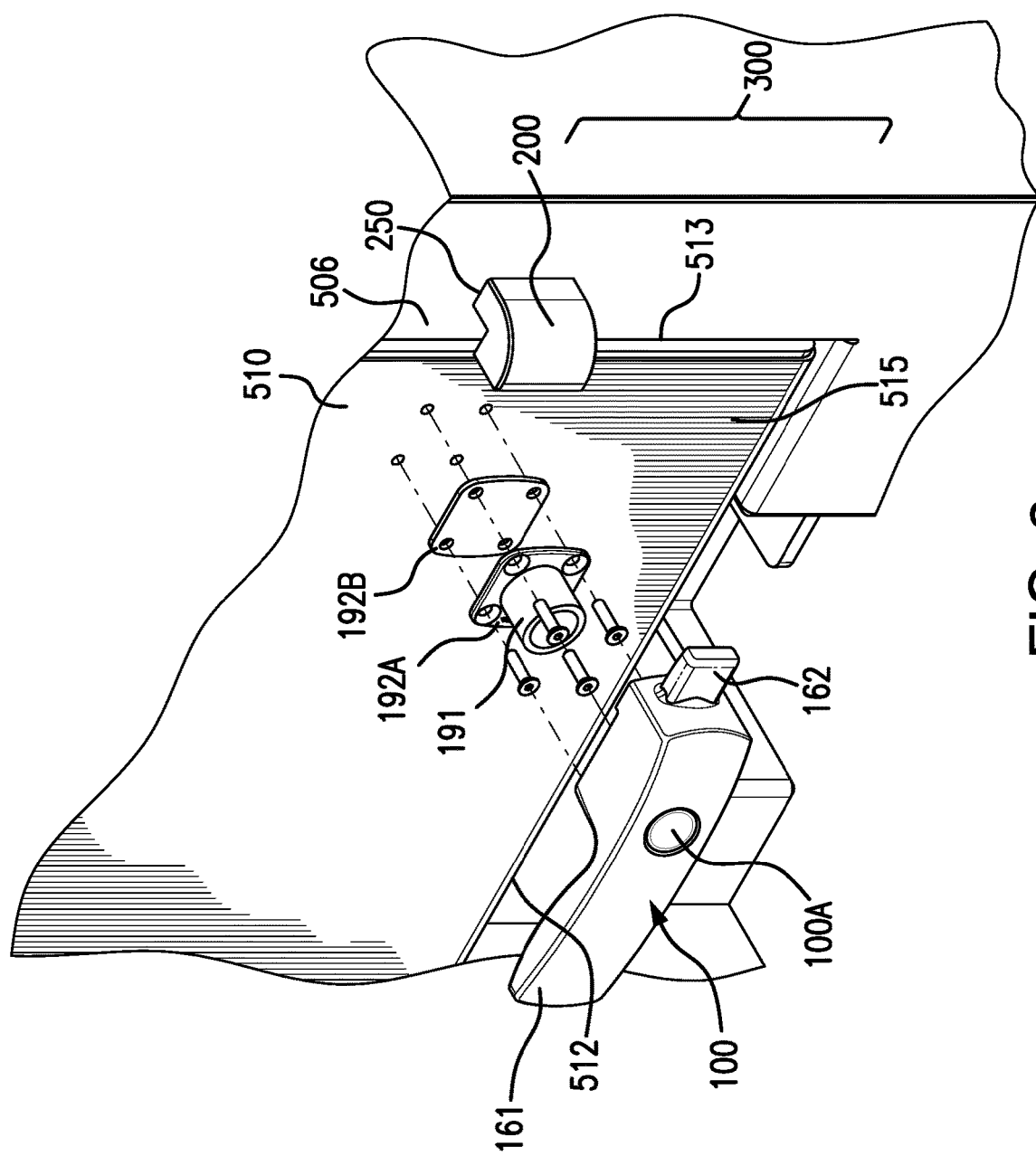
FIG. 2 is a perspective side view showing mounting the rotatable shaft to the hinged tank door.

As is known in the art, there are a number of arrangements and configurations for mounting the rotatable shaft to the door. As shown in FIG. 2, the rotatable shaft 100 rotates around a collar 191 mounted to a flange 192A which is mounted to a gasket 192B mounted to the door. As shown in FIGS. 2 and 3, the door locking mechanism 300 is mounted such that the arm receiver 200 (mounted on the outer surface 515 of the front wall 506 of the tank near the front end 513 of the tank door) is aligned with the rotatable shaft 100, and the projecting arm 162 can be rotated to be received in the receiver top 275 and the arm receiver opening 290, and in some aspects, until the projecting arm contacts the bottom end 286A of the receiver top bottom wall that provides a stop for the projecting arm (see, FIGS. 1C and 4).

While the Figures illustrate the locking mechanism 300 arranged such that the arm receiver is located near the front end 513 of the tank door, other arrangements are within the scope of the invention, for example, the locking mechanism can be arranged such that the arm receiver is located near the top end or bottom end of the tank door.

The rotatable shaft can have a variety of configurations as long as it can be rotatably mounted to the tank door, and the projecting arm can be aligned with the receiver top once the tank door pivots outwardly as described herein. A variety of rotatable shafts are suitable, including commercially available rotatable shafts. If desired, the rotatable shaft can include a safety feature such as a lock button 100A as shown in FIG. 2, wherein the rotatable shaft can only be rotated when the lock button is pushed and held. Suitable rotatable shafts with lock buttons includes those available from, for example, Southco, Inc. (Concordville, Pa.).

In some aspects, the door 510 includes at least one extension 586 providing a door stop preventing the door from entering the internal cavity 520 of the tank. For example, FIG. 5 shows two extensions, 586A, 586B, arranged to contact the front wall 506 preventing the door from entering the internal cavity 520.

Figure 6C:
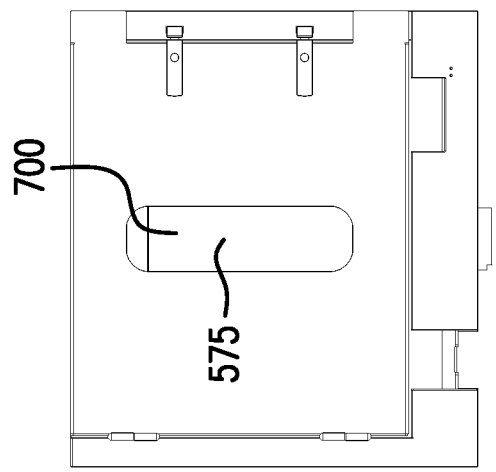
Figure 6B:
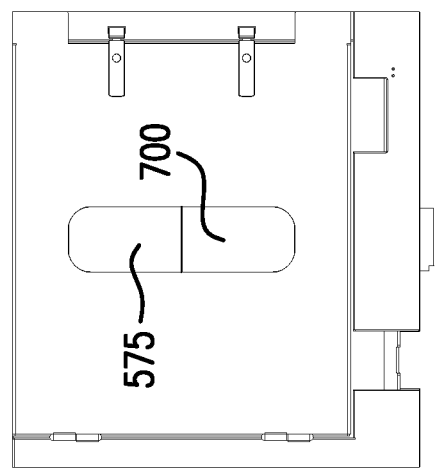
Figure 6A:
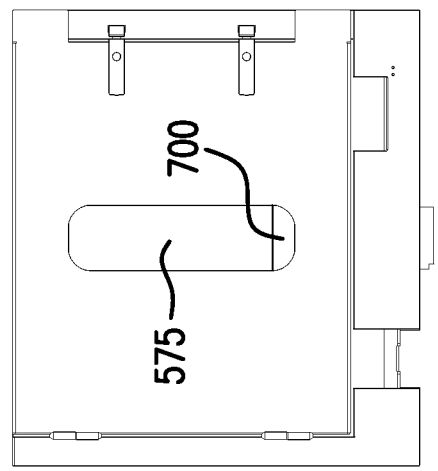

In some aspects, the tank allows the interior to be viewed, e.g., to monitor the filling of the bioprocessing container. For example, FIGS. 5 and 6A-6C show a window 575 in the door 510, wherein FIGS. 6A-6C show the bioprocessing container 700 being filled with liquid. While the bioprocessing container also includes, for example, various fluid ports on the container to allow fluid to enter and exit the container, and, for example, if desired, for sampling the contents of the container and/or venting and/or adding reagents and/or buffers (and tubing is connected to the various fluid ports), for ease of viewing, only a single tube 701A connected to fluid port 701 is shown in FIG. 1F, and FIG. 5 shows bioprocessing container fluid ports 701 and 702, wherein additional tubing and fluid ports are not illustrated.

Figure 9:
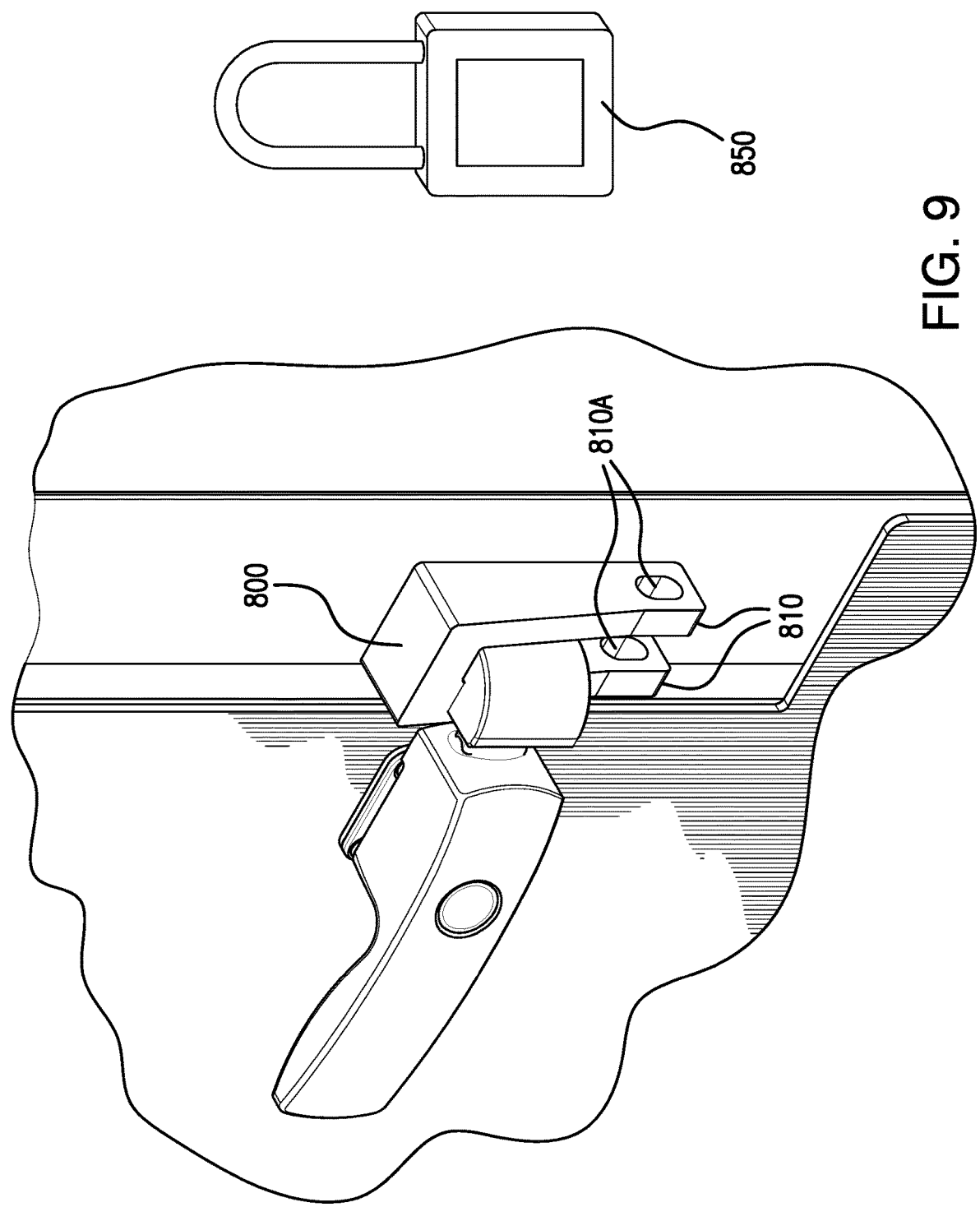
FIG. 9 shows that an external lock can be attached to the locked door locking mechanism shown in FIG. 1C, preventing rotation of the rotatable shaft.

If desired, aspects of the invention can also include a bracket allowing an external lock to be attached to the locked door locking mechanism to reduce the chance that the door would open during transport and/or to prevent unauthorized opening. For example, FIG. 9 shows a bracket 800, illustrated as having a generally "U-shaped" opening allowing the bracket to fit over the arm receiver with the projecting arm received in the arm receiver, wherein the bracket has arms 810 with holes 810A allowing a lock 850 to be mounted to the bracket to prevent opening. If desired, a warning label can be included, e.g., affixed to the lock and/or the bracket.

A variety of bioprocessing containers with flexible walls are suitable for use in aspects of the invention and are commercially available. The bioprocessing containers can have, for example, any suitable shape and volume. Typically, the bioprocessing containers have at least two, and in some aspects, 3 or more, fluid ports, and connected tubing. For example, FIG. 5 shows bioprocessing container fluid ports 701 and 702.

Aspects of the invention include a method of operating the tank with the door locking mechanism during a bioprocessing application. For example, an aspect of the method comprises placing a bioprocessing container with flexible walls into the interior cavity 520 of an aspect of the tank (e.g., including routing bioprocessing container tubing and/or arranging bioprocessing container ports in one or more cutouts such as 805 as shown in FIGS. 1A and 5, and cutout 806 as shown in FIG. 5, and/or in one or more cutouts, e.g., 805A, in the floor 525 as shown in FIGS. 1A, 1D, 1E and 1G); rotating the rotatable shaft until the projecting arm until the projecting arm aligns with the arm receiver opening (see, FIGS. 3 and 1A); filling the bioprocessing container with fluid (see, FIGS. 1F and 6A-6C) until the bioprocessing container expands and a flexible wall of the expanded bioprocessing container contacts the pivoting tank door and the pivoting tank door pivots outwardly (see, FIGS. 1C, and 1E-1G (showing the door pivoted outwardly; FIG. 1F showing an expanded bioprocessing container 700 contacting the tank door causing it to pivot outwardly)).

Depending on the bioprocessing application, after filling the bioprocessing container, one option for bioprocessing includes mixing, wherein a mixer (e.g., a removable mixer drive unit (for example, inserted in an opening 900 in the floor 525 as shown FIG. 1F) or a mixer fixed to the tank through the opening) is activated, powders and/or fluids are added to mix or regulate the product inside the container. Alternatively, or additionally, the tank may include jacketed walls allowing the contents of the bioprocessing container to be heated and/or cooled.

After mixing and/or heating and/or cooling, the bioprocessing container is drained through the drain port. After draining, the bioprocessing container is no longer expanded against the tank door and the rotatable shaft can be rotated upwardly and the door can be opened again and the bioprocessing container can be removed.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A tank with a door locking mechanism comprising:
   (a) the tank comprising a housing having an interior cavity for receiving an expandable bioprocessing container having flexible walls; a bottom wall; a side wall, wherein the side wall has an opening; an outwardly pivoting tank door; and a hinge mounted to the side wall and the outwardly pivoting tank door, wherein the outwardly pivoting tank door is arranged to cover at least a portion of the opening;
   the tank including a door locking mechanism comprising:
      (i) a rotatable shaft mounted to the outwardly pivoting tank door, the rotatable shaft having a first end and a second end, the second end comprising a projecting arm; and,
      (ii) an arm receiver, comprising a base mounted to the at least one side wall of the tank at a distance from the outwardly pivoting tank door and the rotatable shaft, the arm receiver further comprising a receiver top extending horizontally from the base, the receiver top comprising a receiver top wall, first and second opposing receiver top side walls, a receiver top rear wall, and a receiver top front wall having a bottom end, the receiver top opposing side walls each extending toward the base a distance past the bottom end of the receiver top front wall; the bottom end of the receiver top front wall and first and second opposing receiver top side walls defining an arm receiver opening for receiving the projecting arm when the rotatable shaft is rotated to align the projecting arm with the arm receiver opening, and the projecting arm engages with the arm receiving opening as the outwardly pivoting tank door pivots outwardly upon being contacted by the expanded bioprocessing container.

2. The tank with the door locking mechanism of claim 1, wherein the first end of the rotatable shaft comprises a handle.

3. The tank with the door locking mechanism of claim 2, wherein the bottom end of the receiver top front wall provides a stop for the projecting arm.

4. A method of using a tank with the door locking mechanism, the method comprising placing the expandable bioprocessing container with flexible walls into the interior cavity of the tank of claim 3;

rotating the rotatable shaft until the projecting arm until the projecting arm aligns with the arm receiver opening; and, inflating the expandable bioprocessing container with air or gas and/or filling the bioprocessing container with fluid until the expandable bioprocessing container expands and a flexible wall of the expanded bioprocessing container contacts the pivoting tank door and the pivoting tank door pivots outwardly.

5. The tank with the door locking mechanism of claim 1, wherein the bottom end of the receiver top front wall provides a stop for the projecting arm.

6. A method of using a tank with the door locking mechanism, the method comprising placing the expandable bioprocessing container with flexible walls into the interior cavity of the tank of claim 4;

rotating the rotatable shaft until the projecting arm aligns with the arm receiver opening; and, inflating the expandable bioprocessing container with air or gas and/or filling the bioprocessing container with fluid until the expandable bioprocessing container expands and a flexible wall of the expanded bioprocessing container contacts the pivoting tank door and the pivoting tank door pivots outwardly.

7. A method of using a tank with the door locking mechanism, the method comprising placing the expandable bioprocessing container with flexible walls into the interior cavity of the tank of claim 1;

rotating the rotatable shaft until the projecting arm aligns with the arm receiver opening; and, inflating the bioprocessing container with air or gas and/or filling the bioprocessing container with fluid until the expandable bioprocessing container expands and a flexible wall of the expanded bioprocessing container contacts the pivoting tank door and the pivoting tank door pivots outwardly.

8. The method of claim 7, wherein the pivoting door pivots outwardly until the projecting arm contact the bottom end of receiver top front wall.

9. A tank with a door locking mechanism comprising:
   (a) the tank comprising a bottom wall, first and second opposing side walls, a rear wall, an outwardly pivoting tank door, a front wall having an opening, and a hinge mounted to the front wall and the outwardly pivoting tank door, wherein the outwardly pivoting tank door is arranged to cover at least a portion of the opening, the tank having an interior cavity for receiving an expandable bioprocessing container having flexible walls;

the tank including a door locking mechanism comprising:
   (i) a rotatable shaft mounted to the outwardly pivoting tank door, the rotatable shaft having a first end and a second end, the second end comprising a projecting arm; and,
   (ii) an arm receiver, comprising a base mounted to the front wall of the tank at a distance from the outwardly pivoting tank door and the rotatable shaft, the arm receiver further comprising a receiver top extending horizontally from the base, the receiver top comprising a receiver top wall, first and second opposing receiver top side walls, a receiver top rear wall, and a receiver top front wall having a bottom end, the receiver top opposing side walls each extending toward the base a distance past the bottom end of the receiver top front wall; the bottom end of the receiver top front wall and first and second opposing receiver top side walls defining an arm receiver opening for receiving the projecting arm when the rotatable shaft is rotated to align the projecting arm with the arm receiver opening, and the projecting arm engages with the arm receiving opening as the outwardly pivoting tank door pivots outwardly upon being contacted by the expanded bioprocessing container.

10. The tank with the door locking mechanism of claim 9, wherein the first end of the rotatable shaft comprises a handle.

11. The tank with the door locking mechanism of claim 9, wherein the bottom end of the receiver top front wall provides a stop for the projecting arm.

12. A method of using a tank with the door locking mechanism, the method comprising placing the expandable bioprocessing container with flexible walls into the interior cavity of the tank of claim 2;

rotating the rotatable shaft until the projecting arm aligns with the arm receiver opening; and, inflating the expandable bioprocessing container with air or gas and/or filling the bioprocessing container with fluid until the expandable bioprocessing container expands and a flexible wall of the expanded bioprocessing container contacts the pivoting tank door and the pivoting tank door pivots outwardly.

* * * * *